(12) United States Patent
Saito

(10) Patent No.: US 8,708,492 B2
(45) Date of Patent: Apr. 29, 2014

(54) FUNDUS CAMERA AND CONTROL METHOD FOR THE FUNDUS CAMERA

(71) Applicant: Canon Kabushiki Kaisha, Tokyo (JP)

(72) Inventor: Yohei Saito, Chigasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/942,851

(22) Filed: Jul. 16, 2013

(65) Prior Publication Data

US 2013/0301005 A1  Nov. 14, 2013

Related U.S. Application Data

(62) Division of application No. 13/216,393, filed on Aug. 24, 2011, now Pat. No. 8,511,824.

(30) Foreign Application Priority Data

Aug. 31, 2010  (JP) ................................ 2010-194651

(51) Int. Cl.
*A61B 3/14* (2006.01)
*A61B 3/10* (2006.01)
*A61B 3/00* (2006.01)

(52) U.S. Cl.
USPC ........................... 351/206; 351/205; 351/246

(58) Field of Classification Search
USPC .................................................. 351/200–246
See application file for complete search history.

(56) References Cited

U.S. PATENT DOCUMENTS

| 4,690,525 | A | 9/1987 | Kobayashi et al. |
| 5,530,494 | A | 6/1996 | Ogawa et al. |
| 6,244,710 | B1 | 6/2001 | Ogawa |
| 6,832,835 | B2 | 12/2004 | Matsumoto |
| 7,533,990 | B2 | 5/2009 | Hideshima et al. |
| 8,511,824 | B2 * | 8/2013 | Saito ............................ 351/206 |
| 2003/0071966 | A1 | 4/2003 | Matsumoto |
| 2006/0285075 | A1 | 12/2006 | Matsumura |
| 2008/0151189 | A1 | 6/2008 | Iwa et al. |
| 2009/0263115 | A1 * | 10/2009 | Suzuki et al. ................... 396/18 |

FOREIGN PATENT DOCUMENTS

| JP | 60-137347 | A | 7/1985 |
| JP | 61-203937 | A | 9/1986 |
| JP | 02-237536 | A | 9/1990 |
| JP | 03-114434 | A | 5/1991 |
| JP | 04-150831 | A | 5/1992 |
| JP | 05-192299 | A | 8/1993 |
| JP | 06-277184 | A | 10/1994 |
| JP | 08-033612 | A | 2/1996 |

(Continued)

*Primary Examiner* — Mohammed Hasan

(74) *Attorney, Agent, or Firm* — Fitzpatrick, Cella, Harper & Scinto

(57) ABSTRACT

An apparatus including an illumination unit for illuminating an eye to be inspected with light from an observation light source or light from a photographing light source; an photographing unit for guiding reflected light from the eye to an photographing element, to record an image thereof; a calculation unit for calculating an appropriate observation or photographing light intensity based on an illumination light intensity of the illumination unit and an image signal of the photographing element; an automatic light intensity adjustment unit for causing one of the observation and photographing light sources to emit light at the calculated light intensity; and a control unit for controlling the adjustment unit according to a selected one of a mode of acquiring the fundus image and a mode of acquiring the anterior ocular image.

20 Claims, 6 Drawing Sheets

(56) References Cited

FOREIGN PATENT DOCUMENTS

| | | |
|---|---|---|
| JP | 11-238129 A | 8/1999 |
| JP | 2000-107133 A | 4/2000 |
| JP | 2000-197608 A | 7/2000 |
| JP | 2001-258852 A | 9/2001 |
| JP | 2003-010134 A | 1/2003 |
| JP | 2003-116793 A | 4/2003 |
| JP | 2005-261447 A | 9/2005 |
| JP | 2005-261449 A | 9/2005 |
| JP | 2005-270152 A | 10/2005 |
| JP | 2005-279154 A | 10/2005 |

\* cited by examiner

FUNDUS CAMERA AND CONTROL METHOD FOR THE FUNDUS CAMERA

This application is a division of application Ser. No. 13/216,393 filed Aug. 24, 2011 now U.S. Pat. No. 8,511,824 B2.

BACKGROUND OF THE INVENTION

1. Field of the Invention

The present invention relates to a fundus camera for use in taking a fundus image in group medical examination or the like, a control method for the fundus camera, and a program for executing the control method.

2. Description of the Related Art

In taking a fundus image of a subject by a general fundus camera, individual differences in light reflectance of the fundus need to be considered. Obtaining a uniform fundus image thus requires that the emission intensity of a light source be adjusted while observing the fundus. This method, however, takes time to perform photographing or photographing per subject, and is not suitable for group medical examination or other similar situations.

In light of the above, Japanese Patent Application Laid-Open No. 2003-116793 discloses a fundus camera having an automatic light intensity adjustment function, in which an appropriate emission intensity for photographing or photographing is calculated for light emission based on an observation light intensity, the gain of an image signal during observation, and the gain of an image signal during photographing.

Further, some fundus cameras can perform anterior ocular photographing to acquire an image of a peripheral part or iris of an eye to be inspected.

Japanese Patent Application Laid-Open No. H06-277184 discloses a fundus camera which uses an auxiliary lens to perform switching between a fundus mode and an anterior ocular mode.

A general fundus camera has an anterior ocular observation mode of observing the anterior ocular segment of the eye to be inspected in order to perform rough alignment to align a center part of the eye ball with an optical axis, and a fundus mode of observing the fundus portion of the eye to be inspected in order to perform alignment to adjust the eye ball position and the focus position more finely. Obtaining a good fundus image needs observation and adjustment of a photographing light intensity during the alignment. Light reflectance at the fundus portion is, however, different among persons, which needs manual adjustment of the light intensity for each photographing, thus leading to lengthening of inspection time.

In the technology disclosed in Japanese Patent Application Laid-Open No. 2003-116793, the emission intensity for photographing is calculated based on the light intensity and the image signal during observation. Accordingly, when an acquired image greatly changes, such as at the time of switching from anterior ocular observation to fundus observation, there is a large difference between the light intensity calculated for the anterior ocular observation and a necessary light intensity for fundus photographing. Therefore, calculation of the light intensity may take time.

Further, as described above, some fundus cameras, including the one disclosed in Japanese Patent Application Laid-Open No. H06-277184, have an anterior ocular photographing mode which enables photographing of the anterior ocular segment of the eye to be inspected.

In the anterior ocular photographing mode, in consideration of the burden on a subject and the influence on the pupil, a method of illumination with invisible near-infrared light is used in observation for performing alignment. However, in the case of using the automatic light intensity adjustment function which uses an image signal of an image of the anterior ocular segment irradiated with near-infrared light, an appropriate light intensity for photographing with visible light cannot be obtained because reflectance of the iris portion greatly differs between visible light and near-infrared light among racial groups.

SUMMARY OF THE INVENTION

It is therefore an object of the present invention to provide a fundus camera, which is provided with a function capable of controlling automatic light intensity adjustment according to a mode of observation or photographing, to thereby control the automatic light intensity adjustment function according to the mode so that a fundus image with good brightness may be obtained in a short period of time.

In order to achieve the above-mentioned object, a fundus camera for photographing a fundus portion of an eye to be inspected according to an aspect of the present invention includes: an illumination unit including an observation light source for emitting observation light for illuminating the eye to be inspected, and an photographing light source separate from the observation light source, for emitting photographing light for photographing the eye to be inspected, the illumination unit being configured to illuminate the eye to be inspected with one of the observation light and the photographing light; a photographing unit for performing one of observation and photographing of an image of the eye to be inspected by using a photographing element, the photographing element being configured to output an image signal by receiving reflected light from the eye to be inspected, the reflected light resulting from the one of the observation light and the photographing light projected by the illumination unit; a calculation unit for executing calculation of one of an appropriate observation light intensity and an appropriate photographing light intensity based on an illumination light intensity of the illumination unit and the image signal of the photographing element; an automatic light intensity adjustment unit for causing one of the observation light source and the photographing light source to emit light at the light intensity determined by the calculation unit; and a light intensity adjustment control unit having a fundus mode of performing one of observation and photographing of the fundus portion of the eye to be inspected, and an anterior ocular mode of performing one of observation and photographing of an anterior ocular segment of the eye to be inspected, the light intensity adjustment control unit being configured to control the automatic light intensity adjustment unit according to the mode in question.

According to the present invention, the automatic light intensity adjustment function is controlled according to the mode of observation or photographing so that a preferred image of an eye to be inspected may be obtained in a short period of time.

In other words, the fundus camera employing the present invention is capable of obtaining a preferred image of the eye to be inspected in a short period of time, thus enabling photographing with a reduced burden on a subject.

Further features of the present invention will become apparent from the following description of exemplary embodiments with reference to the attached drawings.

DESCRIPTION OF THE EMBODIMENTS

Preferred embodiments of the present invention will now be described in detail in accordance with the accompanying drawings.

First Embodiment

In the following, a fundus camera having a fundus mode, an anterior ocular observation mode, and an anterior ocular photographing mode is described as an example.

Figure 1:
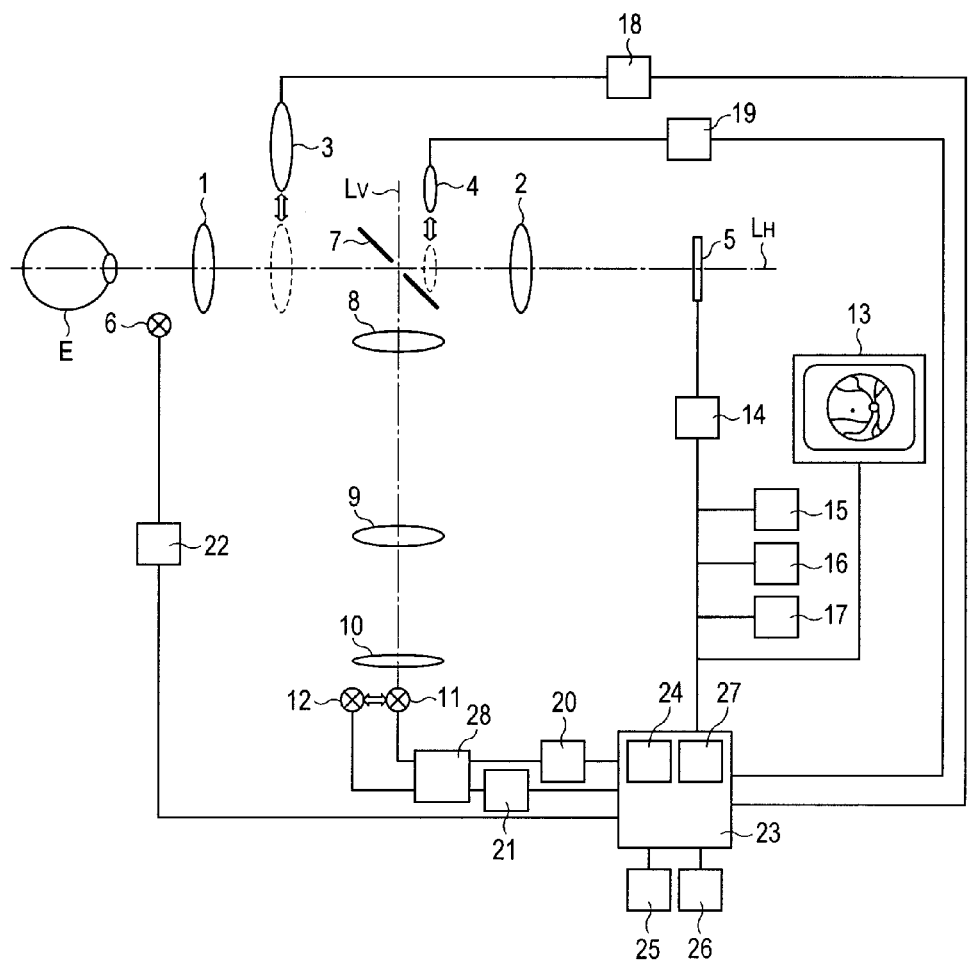
FIG. 1 is a configuration diagram of a fundus camera according to a first embodiment of the present invention.

FIG. 1 is a configuration diagram according to a first embodiment in which the present invention is applied to the fundus camera.

An objective lens 1 is disposed to oppose an eye E to be inspected. On an optical axis (path) $L_H$ of the objective lens 1, there are provided an image-forming lens 2, an anterior ocular observing lens 3 that is insertable and retreatable to and from the optical axis $L_H$, a diopter correction lens 4 that is similarly insertable and retreatable to and from the optical axis $L_H$, and a photographing element 5 having sensitivity to visible light and infrared light. In addition, at a substantially peripheral portion of the objective lens 1, an anterior ocular illumination infrared LED 6 for irradiating the anterior ocular segment of the eye E to be inspected, in particular a peripheral region of the anterior ocular segment, is provided. Further, on the same optical axis $L_H$, an perforated mirror 7 is diagonally provided.

The anterior ocular illumination infrared LED 6 works as an anterior ocular observation light source of the present invention, and emits anterior ocular observation light to illuminate mainly the anterior ocular segment of the eye E to be inspected.

The components from the objective lens 1 to the image-forming lens 2 together constitute an observation optical system. The observation optical system and the photographing element 5 together constitute an observing and photographing unit. The photographing element 5 receives light which is projected by an illumination unit to be described later and the like, namely reflected light which is reflected from the eye E to be inspected. The photographing element 5 then generates and outputs an image signal.

On an optical axis (path) $L_V$ of the perforated mirror 7 in a reflection direction, a lens 8, a lens 9, and a condenser lens 10 are provided. In addition, on the same optical axis $L_V$, a photographing white LED 11 and an observing infrared LED 12 are provided so as to be switchable.

The components from the objective lens 1 to the condenser lens 10 together constitute an illumination optical system. The illumination optical system, the photographing white LED 11 as a photographing light source, and the observing infrared LED 12 as an observation light source together constitute the illumination unit. The photographing white LED 11 emits photographing light for photographing the eye E to be inspected to illuminate the eye E to be inspected. The observing infrared LED 12 emits observation light for observing the eye E to be inspected to illuminate the eye E to be inspected.

The above-mentioned observing and photographing unit and the illumination unit together constitute a fundus camera optical portion. The fundus camera optical portion is placed on a slide table (not shown), enabling alignment with the eye E to be inspected.

An output of the photographing element 5 is converted into a digital signal by an A/D converter element 14. The digital signal is stored in a memory 15 and also connected to a photometry value calculation unit 16. The memory 15 and the photometry value calculation unit 16 are both connected to a control unit (device) 23 for controlling the entire apparatus. The control unit 23 is connected to an image memory 25, and a still image imaged by the photographing element 5 is stored therein as a digital image.

The photographing element 5, the A/D converter element 14, the memory 15, and the photometry value calculation unit 16 as well as a monitor 13 for displaying an infrared observed image and a visible image which are imaged by the photographing element 5 and a photographing unit control portion 17 together constitute an photographing unit. In addition, the photographing unit is fixed to a housing of the fundus camera optical portion via a mount portion (not shown) in a detachable manner.

Movement of the fundus camera is controlled by the control device 23.

The anterior ocular observing lens 3 is inserted and retreated to and from the optical path $L_H$ by an anterior ocular observing lens control unit 18 connected to the control device 23. Further, whether or not the diopter correction lens 4 is present on the optical path $L_H$ is judged by a diopter correction lens position detection unit 19 connected to the control device 23.

The photographing white LED 11 and the observing infrared LED 12 are connected to a light source switching unit 28. Which of the light sources is to be disposed on the optical path $L_V$ is switched by the control unit 23.

A light intensity adjustment control unit 24 is controlled by the control device 23 and performs selection of a light source and selection of a calculation method. A light intensity calculation unit 27 as a calculation unit of the present invention calculates an emission intensity according to a photometry value obtained by the photometry value calculation unit 16 and the light source and the calculation method selected by the light intensity adjustment control unit 24. In other words, the light intensity calculation unit 27 is capable of switching the calculation contents, the calculation method, and the like according to a mode of the light intensity adjustment control unit 24 to be described later, and can be defined as including a calculation switching unit for performing the switching.

A photographing white LED light intensity control unit 20, an observing infrared LED light intensity control unit 21, and an anterior ocular observing infrared LED light intensity control unit 22 cause the photographing white LED 11, the observing infrared LED 12, and the anterior ocular illumination infrared LED 6 to emit light at the light intensities calculated by the light intensity calculation unit 27, respectively.

A photographing switch 26 is connected to the control device 23. When the photographing switch 26 is operated, the above-mentioned control unit causes the respective LEDs as the light source units to emit light at the calculated light intensities so that the observing and photographing unit images an image of the eye to be inspected, which is then recorded.

Next, an actual action of the fundus camera to which the present invention is applied when the automatic light intensity adjustment unit is enabled and used in the fundus mode while the automatic light intensity adjustment unit is disabled and not used in an anterior ocular mode that consists of the anterior ocular observation mode and the anterior ocular photographing mode is described.

Figure 2:
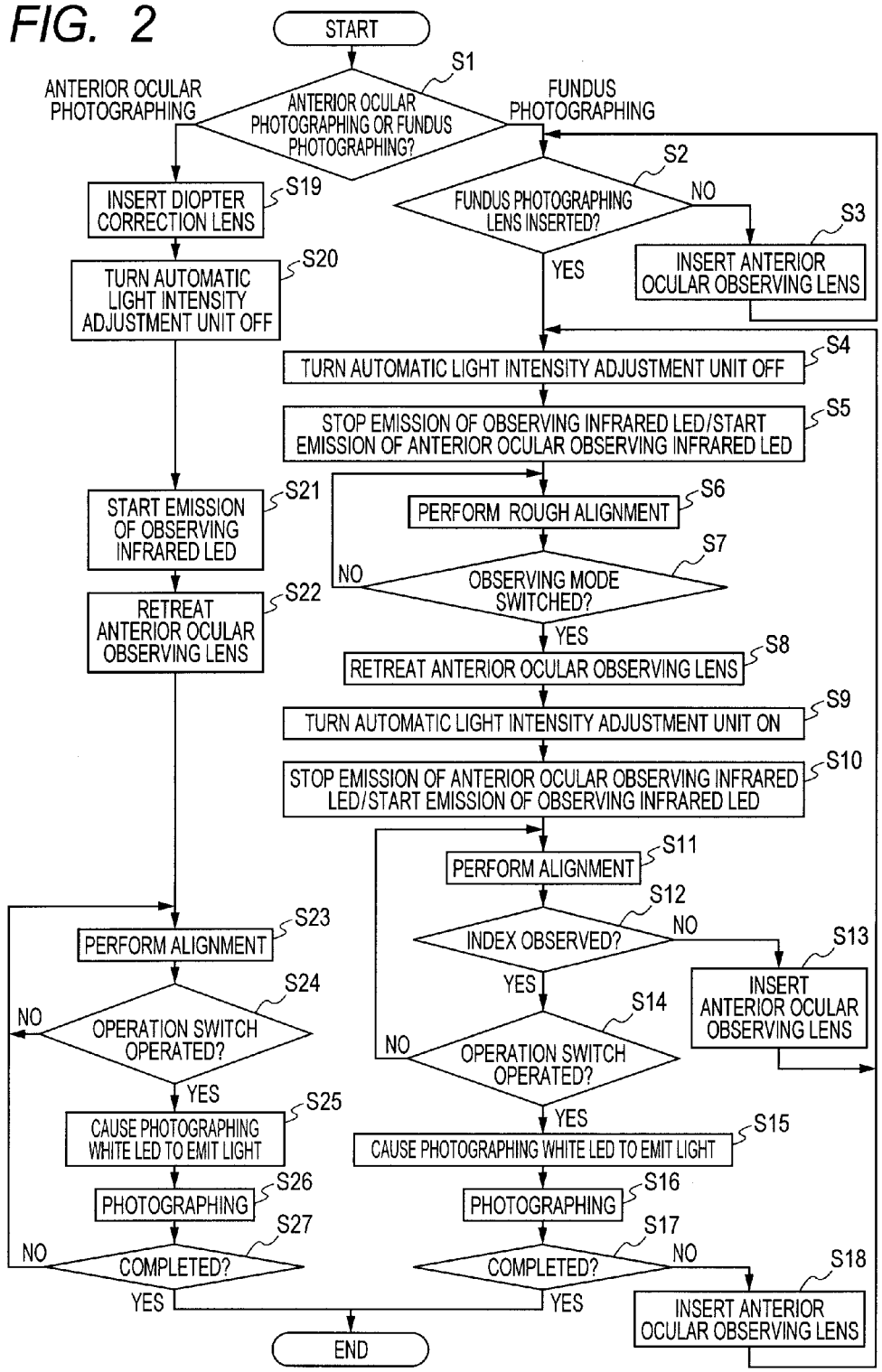
FIG. 2 is a flowchart illustrating an operation of the fundus camera according to the first embodiment.

FIG. 2 is a flowchart for photographing by the fundus camera according to the first embodiment.

In Step S1, which of the anterior ocular photographing and the fundus photographing of the eye to be inspected is to be performed is selected, that is, which of the anterior ocular mode and the fundus mode is to be executed is selected.

In the beginning, an action when the fundus photographing is performed is described.

In Step S2, it is judged whether or not the anterior ocular observing lens 3 is inserted onto the 3 is not inserted onto the optical path $L_H$, the processing proceeds to Step S3, in which the anterior ocular observing lens control unit 18 inserts the anterior ocular observing lens 3, and the mode shifts to the anterior ocular observation mode in the anterior ocular mode. The components related to the shift of the mode, such as the light intensity adjustment control unit 24 and the anterior ocular observing lens control unit 18, work as an anterior ocular observation switching unit together with the light source switching unit, to thereby carry out the switching between the fundus mode and the anterior ocular observation mode.

When the anterior ocular observing lens 3 is inserted, the processing proceeds to Step S4 in synchronization, and the light intensity adjustment control unit 24 disables the photographing white LED light intensity control unit 20, the observing infrared LED light intensity control unit 21, and the anterior ocular observing infrared LED light intensity control unit 22.

At the same time, in Step S5, the emission of the observing infrared LED 12 is stopped and the emission of the anterior ocular observing infrared LED 6 is started.

In Step S6, in order to image the fundus portion of the eye to be inspected, rough alignment between a center part of the eye to be inspected and the optical axis $L_H$ is performed.

In Step S7, it is judged whether or not the rough alignment has succeeded based on a captured image displayed on the monitor 13. When the rough alignment has failed, Step S6 is repeated without shifting the mode.

When the rough alignment has succeeded, the processing proceeds to Step S8, in which the anterior ocular observing lens control unit 18 retreats the anterior ocular observing lens 3 from the optical path $L_H$, and the mode shifts to the fundus mode.

At this time, in Step S9, the photographing white LED light intensity control unit 20, the observing infrared LED light intensity control unit 21, and the anterior ocular observing infrared LED light intensity control unit 22 are enabled to enter the operating state in synchronization with the movement of the anterior ocular observing lens 3. In other words, the light intensity adjustment control unit 24 performs switching control from the disabled state to the enabled state of the light intensity control units as an automatic light intensity adjustment unit.

Further, at the same time, in Step S10, the emission of the anterior ocular observing infrared LED 6 is stopped and the emission of the observing infrared LED 12 is started.

When the mode shifts to the fundus mode, in Step S11, alignment for finer positioning is performed while checking the fundus image on the monitor 13.

In Step S12, it is judged whether or not an index to be used in the alignment is greatly displaced. The alignment index is not observed in an acquired image when the rough alignment position is greatly offset. In this case, the processing proceeds to Step S13, in which the anterior ocular observing lens 3 is inserted onto the optical axis $L_H$ again, and the mode shifts to the anterior ocular observation mode. In this case, as illustrated in Step S4, the photographing white LED light intensity control unit 20, the observing infrared LED light intensity control unit 21, and the anterior ocular observing infrared LED light intensity control unit 22 are disabled in synchronization with the movement of the anterior ocular observing lens 3, and the processing is restarted from rough alignment.

When the index can be confirmed in Step S12, the processing proceeds to Step S14, in which it is judged whether or not photographing is ready. When the photographing is not ready, the processing is restarted from alignment of Step S11.

When it is judged in Step S14 that the photographing is ready, the photographing switch 26 is operated.

In Step S15, in response to the operation of the photographing switch 26 in Step S14, the photographing white LED 11 is caused to emit light.

In Step S16, in synchronization with an emission timing of the photographing white LED 11 in Step S15, the photographing is executed by the photographing unit.

In Step S17, it is judged whether or not to continue the photographing.

In the case of performing continuous photographing, the processing proceeds to Step S18, in which the anterior ocular observing lens is inserted onto the optical path $L_H$, and the mode shifts to the anterior ocular observation mode. After that, the processing proceeds to Step S4, in which the photographing white LED light intensity control unit 20, the observing infrared LED light intensity control unit 21, and the anterior ocular observing infrared LED light intensity control unit 22 are disabled. Further, at the same time, in Step S5, the emission of the observing infrared LED is stopped and the emission of the anterior ocular observing infrared LED is started, thus enabling re-photographing from rough alignment.

Next, an action when the anterior ocular photographing is performed is described.

In Step S19, the diopter correction lens 4 is inserted onto the optical path $L_H$, and the mode shifts to the anterior ocular photographing mode. In this case, the diopter correction lens position detection unit 19 detects that the diopter correction lens 4 is inserted. Note that, in Step S19, the light source switching unit 28 works as an anterior ocular photographing switching unit for carrying out the switching of the mode from the fundus mode to the anterior ocular photographing mode together with the light intensity adjustment control unit 24 and the like.

In synchronization with the detection, in Step S20, the photographing white LED light intensity control unit 20, the observing infrared LED light intensity control unit 21, and the anterior ocular observing infrared LED light intensity control unit 22 are disabled. In other words, the enabled state is switched to the disabled state.

In response to the switching, in Step S21, the emission of the observing infrared LED 12 is started.

Further, at the same time, in Step S22, the anterior ocular observing lens 3 is retreated from the optical path $L_H$.

When the mode shifts to the anterior ocular photographing mode, in Step S23, alignment is performed to move the optical axis $L_H$ to near the center of the position of the anterior ocular segment where an inspector intends to image.

In Step S24, it is judged whether or not the alignment has succeeded. When the alignment has failed, Step S23 is repeated again and alignment is performed in the anterior ocular photographing mode.

When it is judged that the alignment has succeeded, the photographing switch 26 is operated.

When the photographing switch is operated, the processing proceeds to Step S25, in which the photographing white LED 11 is caused to emit light.

In addition, in Step S26, the photographing is executed by the photographing unit in synchronization with an emission timing of the photographing white LED 11.

In Step S27, it is judged whether or not to continue the photographing. In the case of performing continuous photographing, re-photographing can be performed again from alignment.

As described above, the automatic light intensity adjustment function is automatically disabled at the time of switching to the state of acquiring the anterior ocular image. Therefore, the light intensity for observation and photographing of the fundus image is not affected, and hence automatic light intensity adjustment can be performed so that an appropriate light intensity can be obtained in a short period of time.

In other words, when the inspector intends to take a fundus image of the eye to be inspected, the automatic light intensity adjustment function is not used in the anterior ocular observation mode in which rough alignment is performed but is used only for the fundus image. This configuration, which uses the automatic light intensity adjustment only for an image close to the image that the inspector intends to take, enables rapid calculation of the light intensity.

Further, in the anterior ocular photographing mode, a light intensity necessary for the anterior ocular photographing hardly changes, and hence photographing time can be shortened by not using the automatic light intensity adjustment function.

Second Embodiment

The first embodiment has exemplified the configuration of the fundus camera having the fundus mode, the anterior ocular observation mode, and the anterior ocular photographing mode, in which the automatic light intensity adjustment function is disabled at the time of acquiring the anterior ocular image. In this configuration, in the observing and photographing mode, the anterior ocular observation mode and the anterior ocular photographing mode may be switched by a common member, that is, the same member, so as to configure an anterior ocular mode which is common to the anterior ocular observation mode and the anterior ocular photographing mode. Therefore, in this embodiment, the configurations that work as the anterior ocular observation switching unit and the anterior ocular photographing switching unit in the first embodiment are replaced by the control unit 23 and an associated configuration related to the light intensity adjustment as described above.

Figure 3:
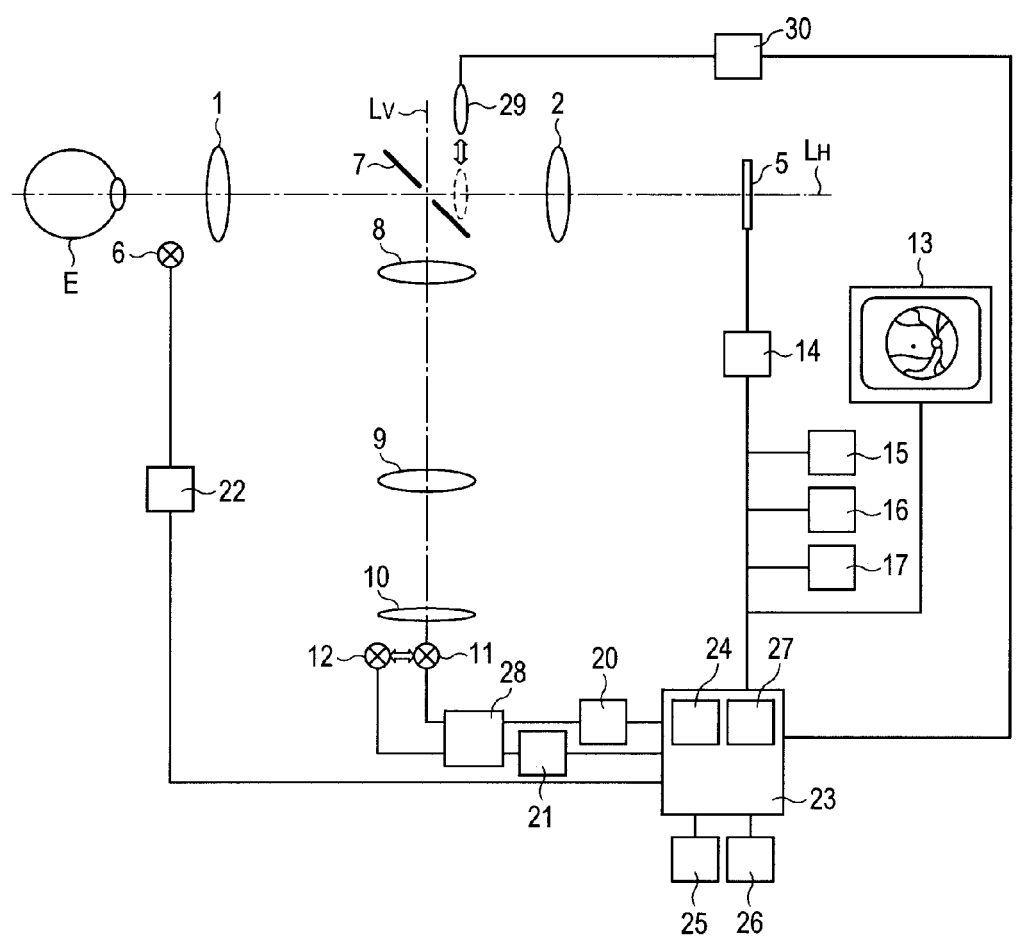
FIG. 3 is a configuration diagram of a fundus camera according to a second embodiment of the present invention.

FIG. 3 is a configuration diagram according to a second embodiment in which the present invention is applied to a fundus camera.

In FIG. 3, the components denoted by the same reference symbols as those of FIG. 1 are equivalent to the components illustrated in the first embodiment.

The anterior ocular observing lens 3 and the diopter correction lens 4 of the first embodiment, which are disposed to be insertable and retreatable to and from the optical path $L_H$ to switch between the anterior ocular observation mode and the anterior ocular photographing mode, are removed. Similarly, the anterior ocular observing lens control unit 18 and the diopter correction lens position detection unit 19 of the first embodiment, which are connected to the control device 23 to respectively control the anterior ocular observing lens 3 and the diopter correction lens 4, are removed from the configuration.

As an alternative to those removed components, the fundus camera of the second embodiment includes an auxiliary lens 29 that is disposed so as to be insertable and retreatable to and from the optical path $L_H$ and an auxiliary lens control unit 30 that is connected to the control device 23 for controlling the auxiliary lens 29.

Next, an action of the fundus camera to which the present invention is applied when automatic light intensity adjustment is used in the fundus mode while the automatic light intensity adjustment is not used in the anterior ocular mode is described.

Figure 4:
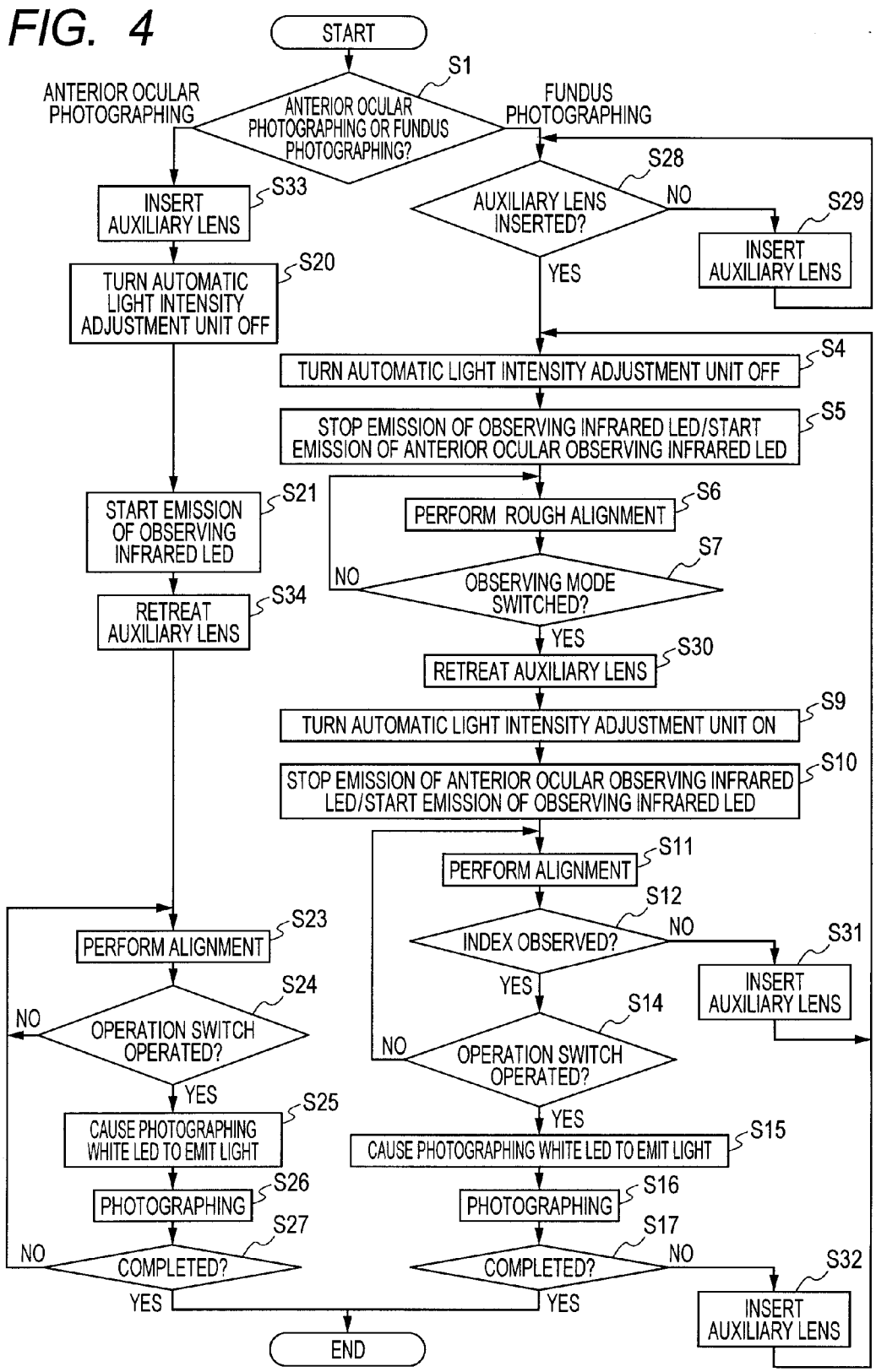
FIG. 4 is a flowchart illustrating an operation of the fundus camera according to the second embodiment.

FIG. 4 is a flowchart for photographing by the fundus camera according to the second embodiment. In FIG. 4, the same reference numerals as those of FIG. 2 denote the same operations as those illustrated in the first embodiment.

In the beginning, a series of flows for fundus photographing is described.

In Step S28, it is judged whether or not the auxiliary lens 29 is inserted onto the optical path $L_H$. When it is judged that the auxiliary lens 29 is not inserted onto the optical path $L_H$, the processing proceeds to Step S29, in which the auxiliary lens control unit 30 inserts the auxiliary lens 29 onto the optical path $L_H$, and the mode shifts to the anterior ocular mode.

When it is judged in Step S28 that the auxiliary lens 29 is inserted onto the optical path $L_H$, the processing proceeds to Step S4 in synchronization, in which the photographing white LED light intensity control unit 20, the observing infrared LED light intensity control unit 21, and the anterior ocular observing infrared LED light intensity control unit 22 are disabled.

When it is judged in Step S7 that the rough alignment has succeeded, the processing proceeds to Step S30, in which the auxiliary lens control unit 30 retreats the auxiliary lens 29 from the optical path $L_H$, and the mode shifts to the fundus mode.

In Step S9, in synchronization with the movement of the auxiliary lens 29, the photographing white LED light intensity control unit 20, the observing infrared LED light intensity control unit 21, and the anterior ocular observing infrared LED light intensity control unit 22 are enabled.

In Step S12, when the alignment position greatly offsets and the alignment index is not observed, the processing proceeds to Step S31. In Step S31, the auxiliary lens 29 is inserted onto the optical path $L_H$ again, and the mode shifts to the anterior ocular mode. At this time, in synchronization thereto, in Step S4, the photographing white LED light intensity control unit 20, the observing infrared LED light intensity control unit 21, and the anterior ocular observing infrared LED light intensity control unit 22 are disabled, and the processing is restarted from rough alignment.

When it is judged in Step S17 to perform continuous photographing, the processing proceeds to Step S32, in which the auxiliary lens 29 is inserted onto the optical path $L_H$, and the mode shifts to the anterior ocular mode. After that, the processing proceeds to Step S4, in which the photographing white LED light intensity control unit 20, the observing infrared LED light intensity control unit 21, and the anterior ocular observing infrared LED light intensity control unit 22 are disabled.

Next, a series of flows for anterior ocular photographing is described.

In Step S33, the auxiliary lens control unit 30 inserts the auxiliary lens 29 onto the optical path $L_H$, and the mode shifts to the anterior ocular mode.

When the auxiliary lens 29 is inserted onto the optical path $L_H$ in Step S33, the processing proceeds to Step S20, in which the photographing white LED light intensity control unit 20, the observing infrared LED light intensity control unit 21, and the anterior ocular observing infrared LED light intensity control unit 22 are disabled. In Step S21, the emission of the observing infrared LED 12 is started. At the same time, in Step S34, the auxiliary lens 29 is retreated from the optical path $L_H$.

As described above, the same effects as those of the first embodiment can be realized with the reduced number of necessary components. Therefore, in addition to the shortening of photographing time exemplified in the first embodiment, cost reduction, simplification of the operation, and the like can be realized.

Third Embodiment

The first and second embodiments have exemplified the configuration in which the automatic light adjustment function is disabled at the time of acquiring an anterior ocular image so as to shorten photographing time. In this configuration, by changing the automatic light adjustment function, automatic light adjustment can be performed in a short period of time. This method is described as a third embodiment of the present invention.

The following description exemplifies a fundus camera which is configured so that automatic light adjustment is performed in the fundus mode while the automatic light adjustment is not performed in the anterior ocular observation mode, and automatic light intensity area adjustment is performed in the anterior ocular photographing mode, which limits an image signal area used for light intensity calculation to the sclera.

The configuration of the third embodiment of the present invention is the same as that illustrated in the first embodiment.

Figure 5:
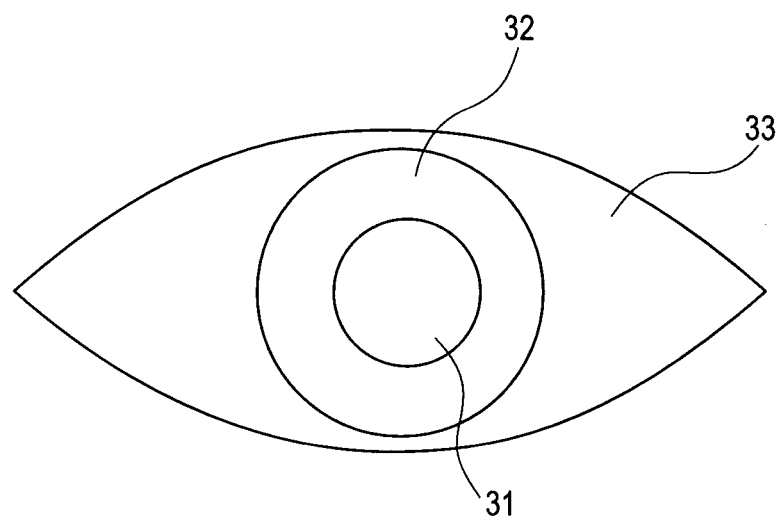
FIG. 5 is a schematic diagram of the anterior ocular segment of an eye to be inspected.

In the beginning, the automatic light intensity area adjustment is described. FIG. 5 schematically illustrates the periphery of the anterior ocular segment, including a pupil portion 31, an iris portion 32, and a sclera portion 33.

The automatic light adjustment function is a function of measuring reflectance of the eye to be inspected based on an emission intensity and an image signal, calculating appropriate light intensities for observation and photographing, and causing any one of the above-mentioned LEDs to emit light at the calculated light intensity. In this function, an image signal from the sclera portion 33, which has little difference in reflectance between visible light and near-infrared light among racial groups, is selected from the acquired image signals to calculate an appropriate light intensity. This corresponds to the automatic light intensity area adjustment.

Next, an action when the automatic light intensity area adjustment is used in the anterior ocular photographing mode is described.

Figure 6:
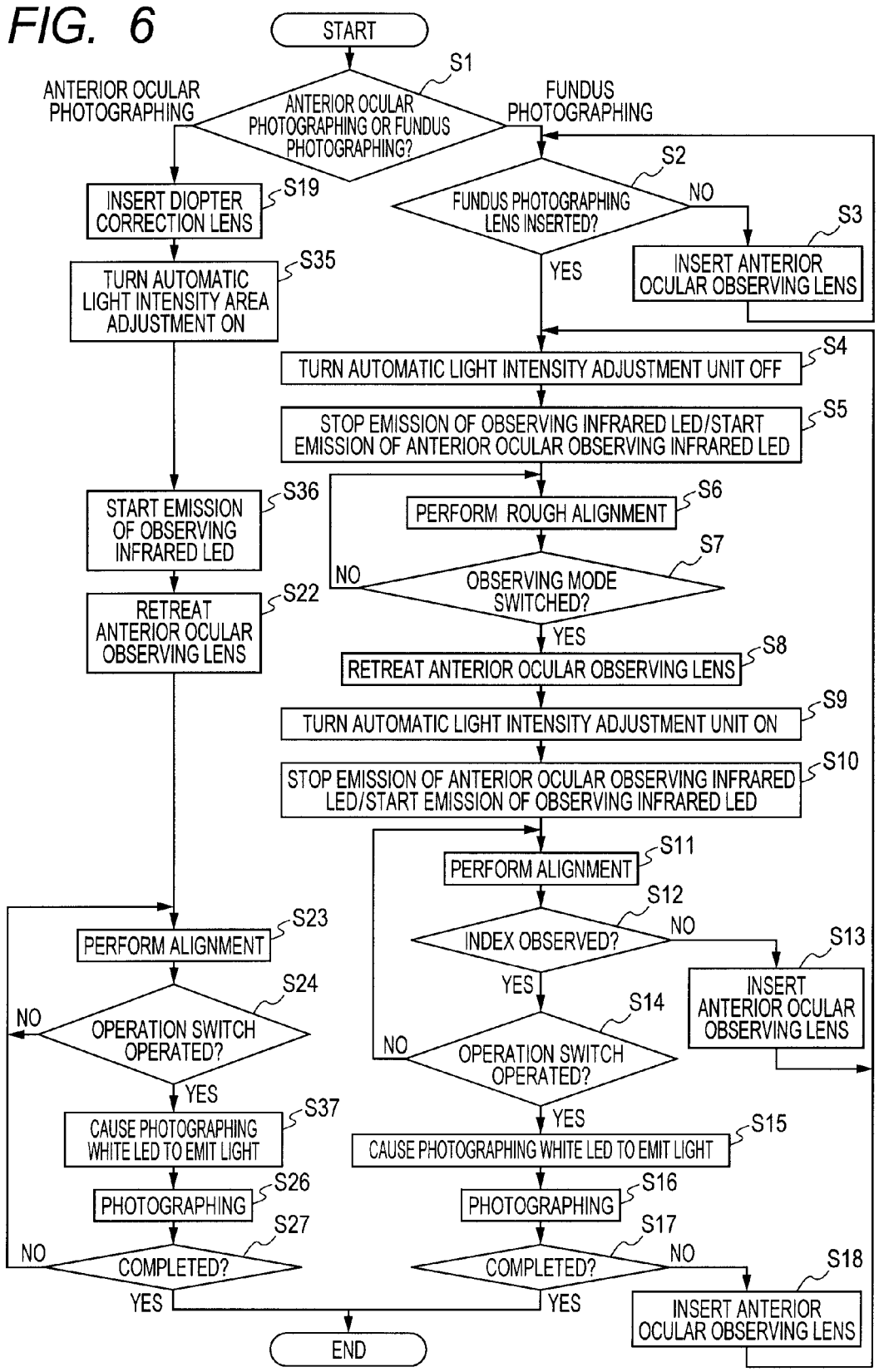
FIG. 6 is a flowchart illustrating an operation of a fundus camera according to a third embodiment of the present invention.

FIG. 6 is a flowchart for photographing by the fundus camera according to the third embodiment. In FIG. 6, the same reference numerals as those of FIG. 2 denote the same operations as those illustrated in the first embodiment.

When it is judged in Step S19 that the diopter correction lens is inserted onto the optical path $L_H$, the processing proceeds to Step S35, in which automatic light intensity area adjustment calculation utilizing the sclera portion of the anterior ocular observed image of the eye to be inspected is performed. The automatic light intensity area adjustment calculation is executed by the light intensity calculation unit 27 as the calculation unit. Then, area calculation is performed, which changes, according to the mode executed by the light intensity adjustment control unit 24, the area of the acquired image signal of the photographing element 5 to be used for calculation. As a result, the photographing white LED light intensity control unit 20, the observing infrared LED light intensity control unit 21, and the anterior ocular observing infrared LED light intensity control unit 22, each of which uses the calculated intensity, are enabled.

In response thereto, in Step S36, the observing infrared LED light intensity control unit 21 starts the emission of the observing infrared LED 12 at the light intensity calculated in the automatic light intensity area adjustment calculation.

Further, in Step S37, the photographing white LED light intensity control unit 20 starts the emission of the photographing white LED 11 at the light intensity calculated in the automatic light intensity area adjustment calculation.

In other words, the above-mentioned calculation switching unit implements calculation corresponding to all the image signals acquired by the photographing element in the fundus mode, and implements calculation by limiting a use range of the image signal to an area suitable for calculation in the anterior ocular mode. Further, it is preferred that the suitable area be an image signal corresponding to the sclera portion of the eye to be inspected as described above.

As described above, instead of using the iris portion or the skin portion, which causes a difference in reflected light intensity of near-infrared light among racial groups, by using the sclera portion, which has little difference in reflected light intensity among racial groups, a suitable image of the eye to be inspected with less variation from person to person can be obtained. In other words, in the anterior ocular photographing mode, at the time of performing automatic light intensity calculation using near-infrared light, instead of using an image signal of the iris portion, which has a difference in reflectance between visible light and near-infrared light among racial groups, by using an image signal of the sclera portion, which less changes the reflectance, an appropriate light intensity for photographing can be obtained.

Other Embodiments

Further, the present invention is also implemented by executing the following processing. Specifically, in this processing, software (program) for implementing the functions of the above-mentioned embodiments is supplied to a system or an apparatus via a network or various kinds of storage medium, and a computer (or CPU, MPU, etc.) of the system or the apparatus reads and executes the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-194651, filed Aug. 31, 2010, which is hereby incorporated by reference herein in its entirety.

What is claimed is:

1. A controlling apparatus for controlling an ophthalmologic apparatus, comprising:
a determining unit for determining, based on an image signal which is output from a photographing unit, at least one of a light intensity of an observation light source and a light intensity of a photographing light source;

an adjustment unit for adjusting, based on the determined light intensity, at least one of a light intensity of the observation light source and a light intensity of the photographing light source; and a control unit for controlling the adjustment unit according to a selection of one of a plurality of modes including at least a fundus mode and an anterior ocular mode.

2. A controlling apparatus for controlling an ophthalmologic apparatus according to claim 1, wherein the control unit disables the adjustment unit in the anterior ocular mode of performing at least one of observation and photographing of an anterior ocular segment of the eye to be inspected, and enables the adjustment unit in the fundus mode of performing at least one of observation and photographing of a fundus portion of the eye to be inspected.

3. A controlling apparatus for controlling an ophthalmologic apparatus according to claim 1, wherein the anterior ocular mode includes (a) an anterior ocular observation mode of observing the anterior ocular segment and (b) an anterior ocular photographing mode of photographing the anterior ocular segment, and wherein the control unit comprises a switching unit for performing one of (a) switching from the fundus mode to the anterior ocular observation mode and (b) switching from the fundus mode to the anterior ocular photographing mode.

4. A controlling apparatus for controlling an ophthalmologic apparatus according to claim 1, wherein the photographing unit performs observation and photographing of an image of the eye to be inspected by using a photographing element, the photographing element being configured to output the image signal by receiving return light from the eye to be inspected, the return light resulting from at least one of the observation light and the photographing light.

5. A controlling apparatus for controlling an ophthalmologic apparatus according to claim 1, wherein the adjustment unit comprises a calculation switching unit for switching the calculation according to the mode, and wherein in the anterior ocular mode, the calculation switching unit changes an area of the image signal to be used for the calculation.

6. A controlling apparatus for controlling an ophthalmologic apparatus according to claim 5, wherein, in the anterior ocular mode, the calculation switching unit performs the calculation by using an area of the image signal corresponding to a sclera portion of the eye to be inspected.

7. A controlling apparatus for controlling an ophthalmologic apparatus, comprising:

a determining unit for determining, based on an image signal which is output from a photographing unit, a light intensity of a light source;

an adjustment unit for adjusting, in a fundus mode, a light intensity of the light source based on the determined light intensity; and a control unit for controlling, in an anterior ocular mode, the adjustment unit so as to manually adjust the light intensity of the light source.

8. A controlling apparatus for controlling an ophthalmologic apparatus according to claim 7, wherein the control unit disables the adjustment unit in the anterior ocular mode of performing at least one of observation and photographing of an anterior ocular segment of the eye to be inspected, and enables the adjustment unit in the fundus mode of performing at least one of observation and photographing of a fundus of an eye to be inspected.

9. A controlling apparatus for controlling an ophthalmologic apparatus according to claim 7, further comprising a switching unit for switching from a fundus photographing mode to an anterior ocular observation mode after the fundus of the eye to be inspected is imaged at the light intensity adjusted by the adjustment unit, wherein the control unit disables the adjustment unit according to the switching made by the switching unit.

10. A controlling method of controlling an ophthalmologic apparatus, the method comprising the steps of:

determining, based on an image signal which is output from a photographing unit, a light intensity of a light source;

adjusting, in a fundus mode, a light intensity of the light source based on the determined light intensity; and controlling, in an anterior ocular mode, the light intensity so as to manually adjust the light intensity of the light source.

11. A recording medium having recorded thereon a program for causing a computer to execute the steps of the controlling method of controlling an ophthalmologic apparatus according to claim 10.

12. A controlling method of controlling an ophthalmologic apparatus according to claim 10, wherein the light intensity adjustment is disabled in the controlling step in the anterior ocular mode of performing at least one of observation and photographing of an anterior ocular segment of an eye to be inspected, and wherein the light intensity adjustment is enabled in the fundus mode of performing at least one of observation and photographing of a fundus of an eye to be inspected.

13. A controlling method of controlling an ophthalmologic apparatus according to claim 10, further comprising a step of switching from a fundus photographing mode to an anterior ocular observation mode after a fundus of the eye to be inspected is imaged at the light intensity adjusted by the adjusting step, wherein the adjustment according to the switching made by the switching step is disabled.

14. A controlling method of controlling an ophthalmologic apparatus, the method comprising the steps of:

determining, based on an image signal which is output from a photographing unit, at least one of a light intensity of an observation light source and a light intensity of a photographing light source which generates photographing light;

adjusting, based on the determined light intensity, at least one of a light intensity of the observation light source and a light intensity of the photographing light source; and controlling the adjustment of the light intensity according to a selection of one of a plurality of modes including at least a fundus mode and an anterior ocular mode.

15. A controlling method of controlling an ophthalmologic apparatus according to claim 14, wherein the adjustment of the light intensity is disabled in the anterior ocular mode of performing at least one of observation and photographing of an anterior ocular segment of an eye to be inspected, and wherein the adjustment of the light intensity is enabled in the fundus mode of performing at least one of observation and photographing of a fundus portion of the eye to be inspected.

16. A controlling method of controlling an ophthalmologic apparatus according to claim 14, wherein the anterior ocular mode includes (a) an anterior ocular observation mode of observing the anterior ocular segment and (b) an anterior ocular photographing mode of photographing the anterior ocular segment, and wherein the controlling step comprises a step of performing one of switching from the fundus mode to the anterior ocular observation mode and switching from the fundus mode to the anterior ocular photographing mode.

17. A controlling method of controlling an ophthalmologic apparatus according to claim 14, wherein observation and photographing of an image of an eye to be inspected is performed by using a photographing element, the photographing element being configured to output the image signal by receiving return light from the eye to be inspected, the return light resulting from at least one of the observation light and the photographing light.

18. A controlling method of controlling an ophthalmologic apparatus according to claim 14, wherein the adjusting step comprises a step of switching the calculation according to the mode, and wherein in the anterior ocular mode, an area of the image signal to be used for the calculation is switched.

19. A controlling method of controlling an ophthalmologic apparatus according to claim 18, wherein, in the anterior ocular mode, the calculation by using an area of the image signal corresponding to a sclera portion of the eye to be inspected is performed by the step of switching.

20. A recording medium having recorded thereon a program for causing a computer to execute the steps of the controlling method of controlling an ophthalmologic apparatus according to claim 14.

* * * * *